(12) United States Patent
Slininger et al.

(10) Patent No.: US 8,569,625 B2
(45) Date of Patent: Oct. 29, 2013

(54) JOINED DISSIMILAR MATERIALS

(75) Inventors: Todd W. Slininger, St. Paul, MN (US);
John W. Warling, Maplewood, MN (US)

(73) Assignee: W. C. Heraeus GmbH, Hanau (DE)

( * ) Notice: Subject to any disclaimer, the term of this patent is extended or adjusted under 35 U.S.C. 154(b) by 369 days.

(21) Appl. No.: 12/644,818

(22) Filed: Dec. 22, 2009

(65) Prior Publication Data
US 2011/0147080 A1    Jun. 23, 2011

(51) Int. Cl.
*H01R 4/18*    (2006.01)

(52) U.S. Cl.
USPC ........................................ 174/88 R; 174/94 R

(58) Field of Classification Search
USPC ................................. 174/88 R, 94 R
See application file for complete search history.

(56) References Cited

U.S. PATENT DOCUMENTS

| | | | |
|---|---|---|---|
| 2,367,206 A * | 1/1945 | Davis | 29/421.2 |
| 3,314,583 A | 4/1967 | Roberts | |
| 3,612,386 A | 10/1971 | Gibson et al. | |
| 3,691,622 A | 9/1972 | Takagi et al. | |
| 3,769,685 A | 11/1973 | Noda | |
| 3,897,896 A | 8/1975 | Louw et al. | |
| 4,811,887 A | 3/1989 | King et al. | |
| 5,368,661 A | 11/1994 | Nakamura et al. | |
| 5,714,103 A | 2/1998 | Bauer et al. | |
| 6,036,725 A | 3/2000 | Avellanet | |
| 6,637,642 B1 | 10/2003 | Lingnau | |
| 6,645,159 B1 | 11/2003 | Burkett | |
| 6,648,206 B2 | 11/2003 | Nelson et al. | |
| 6,779,704 B2 | 8/2004 | Nelson et al. | |
| 6,875,949 B2 | 4/2005 | Hall | |
| 6,918,882 B2 | 7/2005 | Skujins et al. | |
| 7,074,197 B2 | 7/2006 | Reynolds et al. | |
| 7,124,929 B2 | 10/2006 | Nelson et al. | |
| 7,152,776 B2 | 12/2006 | Nelson et al. | |
| 7,270,257 B2 | 9/2007 | Steel et al. | |
| 7,277,762 B2 | 10/2007 | Belden et al. | |
| 7,632,237 B2 | 12/2009 | Murayama et al. | |
| 2004/0039310 A1 | 2/2004 | Burkett | |
| 2004/0167443 A1 | 8/2004 | Shireman et al. | |
| 2005/0035173 A1 | 2/2005 | Steel et al. | |
| 2005/0116012 A1 | 6/2005 | Packer et al. | |

(Continued)

FOREIGN PATENT DOCUMENTS

DE    102006035191 A1    1/2008
DE    102006035191 B4    5/2009

(Continued)

OTHER PUBLICATIONS

Andersen, Olaf, et al., "Direct Typing—a New Method for the Production of Cellular P/M Parts," Proceedings, Euro PM, vol. 4, pp. 1-6 (2004).

(Continued)

*Primary Examiner* — Chau Nguyen
(74) *Attorney, Agent, or Firm* — Dicke, Billig & Czaja, PLLC

(57) ABSTRACT

A wire includes a first wire segment having an end portion and a second wire segment having an end portion. A coupling segment is adjacent the end portions of the first and second wire segments. The coupling segment is configured with a plurality of indents penetrating into at least one of the first and second wire segments.

15 Claims, 2 Drawing Sheets

(56) References Cited

U.S. PATENT DOCUMENTS

| | | |
|---|---|---|
| 2005/0256563 A1 | 11/2005 | Clerc et al. |
| 2006/0047223 A1 | 3/2006 | Grandfield et al. |
| 2006/0122537 A1 | 6/2006 | Reynolds et al. |
| 2006/0204919 A1 | 9/2006 | Thiry |
| 2006/0237407 A1 | 10/2006 | Nguyen et al. |
| 2008/0009934 A1 | 1/2008 | Schneider et al. |
| 2008/0217055 A1 | 9/2008 | Gumley |

FOREIGN PATENT DOCUMENTS

| | | |
|---|---|---|
| EP | 0321796 | 6/1989 |
| EP | 00321796A2 A2 | 6/1989 |
| EP | 0566523 | 10/1993 |
| EP | 0566523 A1 | 10/1993 |
| EP | 0515201 | 9/1997 |
| EP | 1178867 | 9/2004 |
| EP | 1432467 | 12/2005 |
| JP | 2000042744 | 2/2000 |
| JP | 2000042744 A | 2/2000 |
| WO | 9519800 | 7/1995 |
| WO | 9919017 | 4/1999 |
| WO | 0025973 | 5/2000 |
| WO | WO0025973 A1 | 5/2000 |
| WO | 0145578 | 6/2001 |
| WO | 0185384 | 11/2001 |
| WO | 0185385 | 11/2001 |
| WO | 0185385 A1 | 11/2001 |
| WO | WO0185384 A1 | 11/2001 |
| WO | 03030982 | 4/2003 |
| WO | 03030982 A2 | 4/2003 |
| WO | 2005053890 | 6/2005 |
| WO | WO2005053890 A3 | 6/2005 |
| WO | 2006025931 | 3/2006 |
| WO | 2006025931 A1 | 3/2006 |
| WO | 2008014849 | 2/2008 |
| WO | WO2008014849 A1 | 2/2008 |
| WO | 0145578 A2 | 12/2009 |

OTHER PUBLICATIONS

Cohen, Adam L., "EFAB® Technology: Unlocking the Potential of Miniaturized Medical Devices," Microfabrica Inc., pp. 1-31 (2008).

Forschungszentrum Karlsruhe GmbH, "The LIGA-Process (An outline)," Key Technologies, Microsystem Technologies, Fabrication Technologies • Materials, pp. 2 (Sep. 10, 2005). (English Version. pp. 2).

Leonard, Shana, "Welding Technology Fuses Nitinol to Stainless Steel," Medical Device Link (originally published EMDM), pp. 2 (May/Jun. 2007).

\* cited by examiner

JOINED DISSIMILAR MATERIALS

BACKGROUND

The present invention relates to joined dissimilar materials. In one embodiment, the joined materials form a guide wire configured for intravascular use. For example, intravascular guidewires are used in conjunction with intravascular devices such as catheters to facilitate navigation through the vasculature of a patient. Such guidewires are typically very small in diameter. In some applications, a guidewire can have multiple sections that are joined together in order to form a single wire. Joining sections of such a wire having a small diameter can be challenging, particularly where the sections being joined are configured of different materials. Because there are limitations to many present approaches, there is a need for the present invention.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
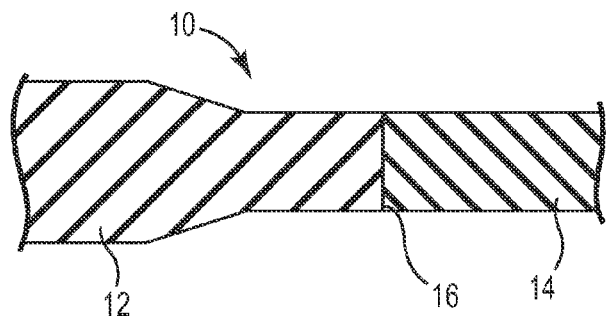
FIG. 1 illustrates a perspective view of a guidewire in accordance with one example.

FIG. 1 illustrates a perspective view of a guidewire 10 in accordance with one embodiment. In one embodiment, guidewire 10 has a proximal section 12 and a distal section 14. In one case, proximal and distal sections 12 and 14 are configured of separate wire segments that are joined together at joint 16. In some embodiments, proximal and distal sections 12 and 14 are adapted with differing diameter regions, are adapted and configured to obtain a transition in stiffness, and provide a desired flexibility characteristic. In FIG. 1, guidewire 10 is illustrated with a truncation in its ends, as its length may vary in accordance with particular applications.

As used herein, the proximal section 12 and the distal section 14 can generically refer to any two adjacent wire sections along any portion of guidewire 10. Furthermore, although discussed with specific reference to guidewires, the wire segments can be applicable to almost any intravascular device. For example, they are applicable to hypotube shafts for intravascular catheters (e.g., rapid exchange balloon catheters, stent delivery catheters, etc.) or drive shafts for intravascular rotational devices (atherectomy catheters, IVUS catheters, etc.).

In one example, proximal section 12 can be configured of a relatively stiff material, such as stainless steel wire. Alternatively, proximal section 12 can be comprised of a metal or metal alloy such as a nickel-titanium alloy, nickel-chromium alloy, nickel-chromium-iron alloy, cobalt alloy, or other suitable material. In general, the material used to construct proximal section 12 can be selected to be relatively stiff for pushability and torqueability.

Also, in some embodiments, distal section 14 can be configured of a relatively flexible material, such as a super elastic or linear elastic alloy) wire, such as linear elastic nickel-titanium (NiTi), or alternatively, a polymer material, such as a high performance polymer. Alternatively, distal section 14 can be configured of a metal or metal alloy such as stainless steel, nickel-chromium alloy, nickel-chromium-iron alloy, cobalt alloy, or other suitable material. In general, the material used to configure distal section 14 can be selected to be relatively flexible for trackability.

Figure 2:
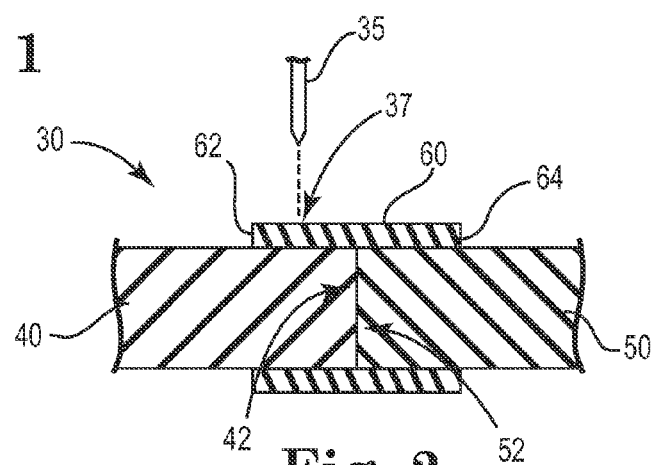
FIG. 2 illustrates a cross sectional view of joined dissimilar materials in accordance with one embodiment.

FIG. 2 illustrates a cross-sectional view of guide wire 30 in accordance with one embodiment. In one embodiment, guidewire 30 includes first wire section 40, second wire section 50 and coupler 60. In one example, guidewire 30 is configured for use in conjunction with intravascular devices, such that first wire section 40 has relatively stiff characteristics for pushability and torqueability, and such that second wire section 50 has relatively flexible characteristics for trackability.

In one embodiment, first and second sections 40 and 50 are formed of different wire segments and joined together using coupler 60. In one example, a first end 42 of first wire section 40 is placed inside a first end 62 of coupler 60 and a first end 52 of second wire section 50 is placed inside a second end 64 of coupler 60. In one case, first ends 42 and 52 are pushed together inside coupler 60 such that they are immediately adjacent, for example, so that they touch. Coupler 60 can help facilitate the joining of first and second wire sections 40 and 50.

In one embodiment, the joining of first and second wire sections 40 and 50 includes the use of a laser 35, such as a YAG laser or a fiber laser. In one embodiment, a laser beam from laser 35 is applied directly to coupler 60 in a target area 37 of coupler 60. When the laser 35 is energized such that the beam is directed to coupler 60, area 37 is melted. In turn, the melted material in area 37 of coupler 60 will partially melt portions of first and second wire sections 40 and 50 that are immediately adjacent area 37 of coupler 60. In one embodiment, laser 35 is configured to apply a beam to coupler 60 that is perpendicular to guidewire 30. In operation, guidewire 30 is pushed and pulled along its axis, such that laser 35 is applied perpendicular to these applied loads. This perpendicular application results in a strong hold between first and second wire sections 40 and 50 and coupler 60, as explained below.

Figure 3:
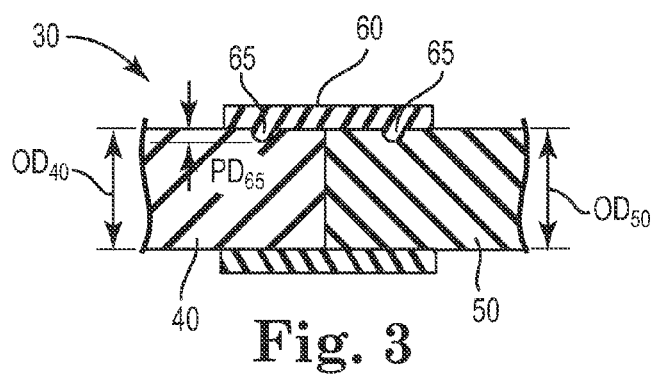
FIG. 3 illustrates a cross sectional view of joined dissimilar materials with indents in accordance with one embodiment.

FIG. 3 illustrates guidewire 30 with first wire section 40 and second wire section 50 within coupler 60. In the illustration, first wire section 40 has an outer diameter $OD_{40}$ and second wire section 50 has an outer diameter $OD_{50}$. In FIG. 3, a plurality of indents 65 are formed. In the embodiment, each of indents 65 penetrate into either first or second wire sections 40 or 50 to a penetration depth $PD_{65}$.

In one embodiment, after coupler 60 is fitted over first and second wire sections 40 and 50, laser 35 (FIG. 2) is used to melt areas of coupler 60 such that indents 65 are created from coupler 60. Indents 65 penetrate down into first and second wire sections 40 and 50. When the laser beam of laser 35 is applied to coupler 60, areas (37 in FIG. 2) of the material of coupler 60 impacted by the laser 35 are melted. In turn, these melted areas of coupler 60 partially melt the first and second wire sections 40 and 50 adjacent that melted areas of coupler 60, illustrated in FIG. 3 as indents 65. The resulting indents 65, in conjunction with coupler 60, provide a secure mechanical connection between first and second wire sections 40 and 50.

In one embodiment, there are small spaces between the outer diameters of first and second wire sections 40 and 50 and the inner diameter of coupler 60. In one embodiment, as material in these areas turns molten with the application of a laser beam, the molten material will tend to fill this space. In such cases, indent 65 can have a slightly "saddle" shape as the molten material flows down the sides of the cylindrical wire sections 40 and 50.

In one example, first wire section 40 is a segment of stainless steel wire, second wire section 50 is a segment of linear elastic nickel-titanium (NiTi) alloy, such as nickel-titanium wire, and coupler 60 is a stainless steel hypotube. As such, in that case, indents 65 are also stainless steel from coupler 60 that is forced down into first and second wire sections 40 and 50 upon welding. A guidewire 30 configured in this way allows first wire section 40 to have a relatively stiff characteristics for pushability and torqueability, and allows second wire section 50 to have a relatively flexible characteristics for trackability.

In one embodiment, because coupler 60 has a snug fit over first and second wire sections 40 and 50 while laser 35 is used to melt areas of coupler 60, first and second wire sections 40 and 50 are well secured linearly such that they are prevented from relative movement during welding. Much of the shear forces or bending moments between first and second wire sections 40 and 50 are eliminated while they are stabilized by the tight fitting coupler 60. Shear or bending forces between first and second wire sections 40 and 50 during a weld will tend to degrade the weld. Coupler 60 can help limit or avoid such shear and bending forces. As such, indents 65 generated via these welds tend to be more secure than would welds made where there is even slight movement between first and second wire sections 40 and 50.

Also in one embodiment, the beam of laser 35 is applied directly to coupler 60, and not directly to either first or second wire sections 40 or 50. In the case where coupler 60 is a segment of stainless steel wire and second wire section 50 is a segment of linear elastic nickel-titanium (NiTi) alloy, the beam of laser 35 will directly impact only the stainless steel and will not directly impact the nickel-titanium. The nickel-titanium will only be indirectly impacted from the melting of adjacent stainless steel in coupler 60 (which receives the direct laser beam). In some embodiments, weaknesses within the nickel-titanium are avoided by avoiding welding with the beam of laser 35 directly on the nickel-titanium material.

In one embodiment, power levels of laser 35 are controlled such that the penetration depth $PD_{65}$ of indents 65 is limited. If indents 65 are allowed to penetrate too deep into first and second wire sections 40 and 50 upon welding, weakness can be introduced into the sections adjacent indent 65. In one case, the penetration depth $PD_{65}$ of indents 65 is limited to less the 50% of the outer diameters $OD_{40}$ and $OD_{50}$ of first and second wire sections 40 and 50. In yet another embodiment, penetration depth $PD_{65}$ of indents 65 is limited to less the 20% of the outer diameters $OD_{40}$ and $OD_{50}$ of first and second wire sections 40 and 50 to even further limit any weakness introduced into the sections.

The illustrated guidewire 30 can be configured in a variety of sizes in accordance with various embodiments. In one example, diameters $OD_{40}$ and $OD_{50}$ of first and second wire sections 40 and 50 can range from about 0.005 to about 0.02 inches. In one example, indents 65 are produced with the application of laser welds, where the penetration depth $PD_{65}$ of indents 65 is limited in the range of about 0.0025 to about 0.01 inches. In another example, indents 65 are produced with the application of laser welds, where the penetration depth $PD_{65}$ of indents 65 is limited in the range of about 0.001 to about 0.004 inches.

Fusion welding of nickel alloy and titanium alloy has challenges, for example, issues of solidification and cracking due to intermetallic formation. Limiting the depth of indents 65 in accordance with embodiments also limits the amount of mixture that occurs between the materials that make up coupler 60 and first and second wire sections 40 and 50, thereby limiting intermetallic formation.

For example, when coupler 60 is stainless steel and second wire section 50 is nickel-titanium wire, excessive mixture of these materials in molten states will create brittle intermetallic phases from the combination of stainless steel and nickel-titanium. Examples of such brittle intermetallic phases include: $Fe_2Ti$, $FeTi$, $FeTi_2$, $FeTiO_4$, and $TiC$. Creation of excessive amounts of brittle intermetallic phases will weaken wire sections 40 and 50 in these areas where they are created.

In one embodiment, although indents 65 represent some amount of mixing of the materials that make up coupler 60 and either first or second wire sections 40 or 50, controlling and limiting the power used for laser 35 limits the penetration depth $PD_{65}$ of indents 65 and also minimizes the brittle intermetallic phases created in the area. In this way, this tends to maximize the strength of first and second wire sections 40 and 50.

In one example, coupler 60 is stainless steel and second wire section 50 is nickel-titanium. The power used for laser 35 is controlled and limited during the formation of indents 65 such that mixture molten stainless steel and molten nickel-titanium is minimized, as is the creation of brittle intermetallic phases. As such, brittle intermetallic phases, such as $Fe_2Ti$, $FeTi$, $FeTi_2$, $FeTiO_4$, and $TiC$, are less than 30 percent of the total material in indent 65.

Although FIG. 3 illustrates one indent 65 in each of first and second wire sections 40 and 50, in some embodiments, two indents 65 are formed in each of first and second wire sections 40 and 50, and in yet other embodiments more than two indents 65 are in each section. In one embodiment, coupler 60 is welded in a spiral pattern such that indents 65 are likewise distributed in a spiral pattern about first and second wire sections 40 and 50. This produces a secure mechanical hold between the wire sections 40 and 50. Other patterns and distributions for indents 65 are also possible.

In one embodiment, after coupler 60 is welded to produce indents 65, guidewire 30 and especially coupler 60 can be ground to decrease the outer diameter of guidewire 30 in the area of coupler 60. In one example, guidewire 30 can be ground such that substantially no portion of coupler 60 extends beyond the outer diameter of guidewire 30.

Figure 4:
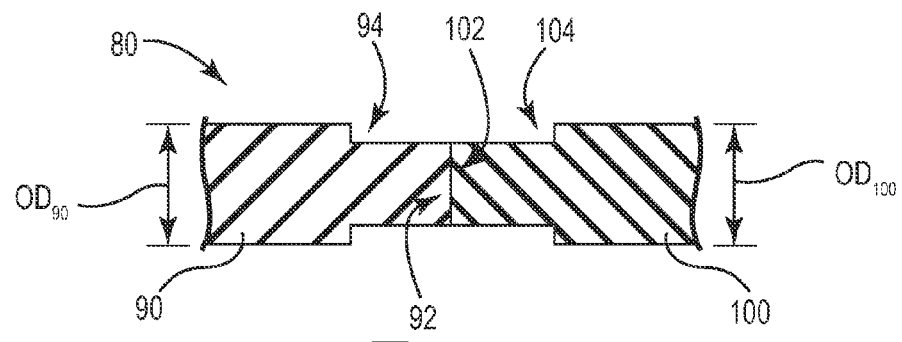
FIG. 4 illustrates a cross sectional view of joined dissimilar materials with a recess in accordance with one embodiment.

FIG. 4 illustrates a cross-sectional view of guidewire 80 in accordance with one embodiment. In one embodiment, guidewire 80 includes first wire section 90 and second wire section 100 with respective ends 92 and 102. First wire section 90 includes recess 94 adjacent end 92 and second wire section 100 includes recess 104 adjacent end 102. In areas outside of recess 94, first wire section 90 has an outer diameter $OD_{90}$. Recess 94 is recessed relative to the outer diameter $OD_{90}$ of first wire section 90. Similarly, in areas outside of recess 104, second wire section 100 has an outer diameter $OD_{100}$. Recess 104 is recessed relative to the outer diameter $OD_{100}$ of second wire section 100.

Figure 5:
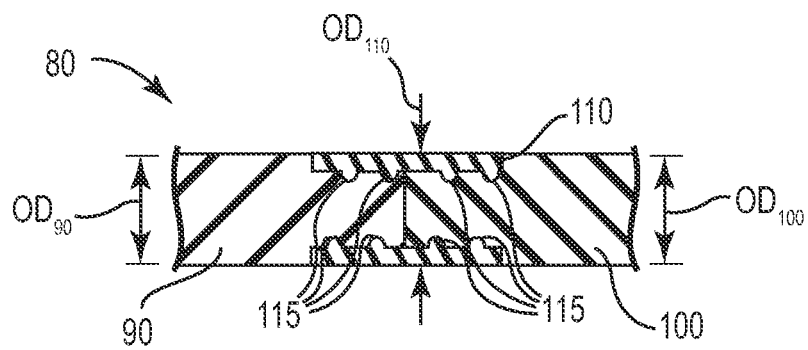
FIG. 5 illustrates a cross sectional view of joined dissimilar materials with indents in accordance with one embodiment.

When first and first ends 92 and 102 are placed immediately adjacent, recesses 94 and 104 align. In one embodiment, coupler 110 fits over the aligned recesses 94 and 104, as illustrated in FIG. 5. In one embodiment, the thickness of coupler 110 is matched with the depth of recesses 94 and 104 such that the outer diameters $OD_{90}$ and $OD_{100}$ of first and second wire sections 90 and 100 are equal to the outer diameter $OD_{110}$ of coupler 110. In this way, the overall outer diameter of guidewire 80 is constant, in one embodiment.

Although the transitions from recesses 94 and 104 to the outer diameters $OD_{90}$ and $OD_{100}$ are illustrated as sharp, such that the transitions are essentially vertical, other transitions are also possible in accordance with other embodiments. For example, in another embodiment the transitions from recesses 94 and 104 to the outer diameters $OD_{90}$ and $OD_{100}$ are gradual such that the transitions appear more as a ramp, rather than vertical. In that case, coupler 110 is also gradually tapered at its ends to match the gradual transitions from recesses 94 and 104 to the outer diameters $OD_{90}$ and $OD_{100}$.

With coupler 110 placed in recesses 94 and 104, a plurality of indents 115 are formed with a laser, such as described above with laser 35. In the embodiment, each of indents 115 penetrate into either first or second wire sections 90 or 100. In one embodiment, after coupler 110 is fitted over first and second wire sections 90 and 100, a laser is directed at areas of coupler 110 such that indents 115 are created from coupler 110 and penetrate down into first and second wire sections 90 and 100.

Coupler 110 and indents 115 can help facilitate the joining of first and second wire sections 90 and 100. In one example, first wire section 90 is a segment of stainless steel wire, second wire section 100 is a segment of linear elastic nickel-titanium (NiTi) alloy, and coupler 110 is a stainless steel hypotube. As such, in that example, indents 115 represent some amount of mixing of the stainless steel of coupler 110 and the nickel-titanium of either first or second wire sections 90 or 100 upon welding. In one embodiment, the power used for laser welding is controlled to limits the penetration depth of indents 115 and minimizes the brittle intermetallic phases created in the area, as discussed above in conjunction with guidewire 30.

Also similar to guidewire 30 above, the penetration depth of indents 115 is limited to less the 50% of the outer diameters $OD_{90}$ and $OD_{100}$ of first and second wire sections 90 and 100. In yet another embodiment, the penetration depth of indents 115 is limited to less the 20% of the outer diameters $OD_{90}$ and $OD_{100}$ of first and second wire sections 90 and 100 to even further limit any weakness introduced into the sections.

In one embodiment, guidewire 80 is configured for use in conjunction with intravascular devices, such that first wire section 90 has relatively stiff characteristics for pushability and torqueability, and such that second wire section 100 has relatively flexible characteristics for trackability.

Figure 6:
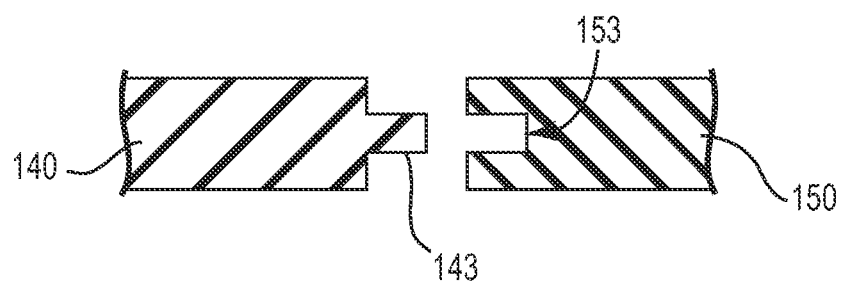
FIG. 6 illustrates a cross sectional view of two dissimilar materials in accordance with one embodiment.

FIG. 6 illustrates a cross-sectional view of first and second wire sections 140 and 150. First wire section 140 includes extension 143 and second wire section 150 includes notch 153. Guidewire 130 is then formed when extension 143 is placed in notch 153 thereby joining first and second wire sections 140 and 150 as illustrated in FIG. 7.

Figure 7:
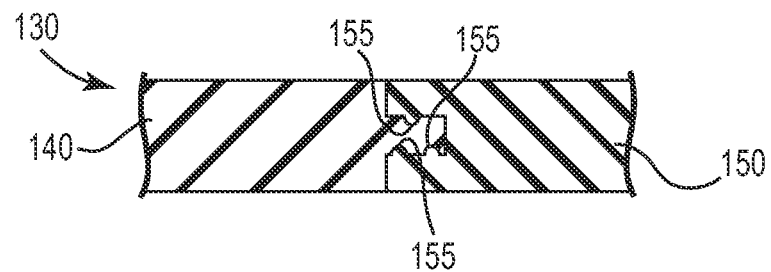
FIG. 7 illustrates a cross sectional view of joined dissimilar materials with indents in accordance with one embodiment.

Also illustrated in FIG. 7 are indents 155 formed in guidewire 130. In one embodiment, each of indents 155 penetrates from second wire section 150 into first wire section 140, and specifically, penetrates into extension 143 of first wire section 140. In one embodiment, after extension 143 is placed in notch 153, a laser is used to weld into second wire section 150 adjacent extension 143 such that indents 155 are created from second wire section 150 and penetrate down into first wire section 140.

In the embodiment illustrated in FIG. 7, no coupling device separate from first and second wire sections 140 and 150 is used. Instead, the portions of second wire section 150 that extend beyond notch 153 function as the couplers 60 (FIG. 3) and 110 (FIG. 5) did in the above-described embodiments. In this way, indents 155, along with the fit of extension 143 within notch 153, can help facilitate the secure joining of first and second wire sections 140 and 150.

In one embodiment, first wire section 140 is a segment of linear elastic nickel-titanium (NiTi) alloy, and second wire section 150 is a segment of stainless steel wire. In one embodiment, the laser used to generate indents 155 is applied directly to second wire segment 150, and not directly to first wire section 140. In this embodiment where second wire segment 150 is a segment of stainless steel wire and first wire section 140 is a segment of linear elastic nickel-titanium (NiTi) alloy, the laser beam will directly impact only the stainless steel and will not directly impact the nickel-titanium, thereby avoiding weakness within associated with direct welding of the nickel-titanium, as described above.

As with the prior-described embodiments, power to the laser used to create indents 155 is controlled to limit the penetration depth of the indents and to limit the amount of mixture between the stainless steel of second wire segment 150 and the nickel-titanium of first wire section 140, thereby limiting brittle intermetallic phases created. In one embodiment, the penetration depth of indents 115 is limited to less than 50% of the outer diameters of first and second wire sections 140 and 150, and in another limited to 20%. In one embodiment, no more than 30 percent of the material of indents 155 is brittle intermetallic phases.

In one embodiment, guidewire 130 is configured for use in conjunction with intravascular devices, such that second wire section 150 has relatively stiff characteristics for pushability and torqueability, and such that first wire section 140 has relatively flexible characteristics for trackability.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A wire comprising:
   a first wire segment having an end portion;
   a second wire segment having an end portion, one of the first and second wire segments comprising a first material; and
   a coupling segment comprising a second material and adjacent the end portions of the first and second wire segments, and wherein the coupling segment is configured with at least one indent penetrating into at least one of the first and second wire segments, wherein the indent comprises a mixture of the first material from the first or second wire segment and the second material from the coupling segment, and wherein the mixture of the first material from the first or second wire segment and the second material from the coupling segment is such that no more than 30 percent of the materials in the indents are brittle intermetallic phases.

2. The wire of claim 1 wherein the coupling segment is a tubular coupler separate from the first and second wire segments into which the first and second wire segments are inserted.

3. The wire of claim 2, wherein a plurality of indents penetrates into each of the first and second wire segments from the coupling segment.

4. The wire of claim 1, wherein the wire has an outer diameter, wherein the indent penetrates a penetration distance into one of the first and second wire segments, and wherein the penetration distance is no more than fifty percent of the wire outer diameter.

5. The wire of claim 4, wherein the wire has an outer diameter, wherein the indent penetrates a penetration distance into one of the first and second wire segments, and wherein the penetration distance is no more than twenty percent of the wire outer diameter.

6. The wire of claim 1, wherein the indent is formed by welding the coupling segment with a laser such that a laser beam is applied directly to the coupling segment and such that the laser is not applied directly to either the first or second wire segments.

7. The wire of claim 6, wherein the laser beam is applied to the coupling segment in a direction that is transverse to the axial length of the wire.

8. The wire of claim 6, wherein the coupling segment is laser welded along a spiral path around at least one of the first and second segments.

9. The wire of claim 1, wherein the second material of the coupling segment comprises stainless steel and the first material of either the first or second wire segments comprises nickel-titanium.

10. The wire of claim 1, wherein the outer diameter of the wire is between 0.005 and about 0.02 inches.

11. A wire comprising:
a first wire segment having an end portion;
a second wire segment having an end portion, one of the first and second wire segments comprising a first material; and
a coupling segment comprising a second material and adjacent the end portions of the first and second wire segments, and wherein the coupling segment is configured with at least one indent penetrating into at least one of the first and second wire segments, wherein the indent comprises a mixture of the first material from the first or second wire segment and the second material from the coupling segment, wherein the coupling segment is a tubular coupler separate from the first and second wire segments into which the first and second wire segments are inserted, wherein the first wire segment has a first outer diameter away from the end portion and a second outer diameter adjacent the end portion, the first outer diameter greater than the second outer diameter, wherein the second wire segment has a first outer diameter away from the end portion and a second outer diameter adjacent the end portion, the first outer diameter greater than the second outer diameter, and wherein the tubular coupler has an outer diameter substantially equal to the first outer diameters of the first and second wire segments.

12. A wire comprising:
a first wire segment having an end portion;
a second wire segment having an end portion, one of the first and second wire segments comprising a first material; and
a coupling segment comprising a second material and adjacent the end portions of the first and second wire segments, and wherein the coupling segment is configured with at least one indent penetrating into at least one of the first and second wire segments, wherein the indent comprises a mixture of the first material from the first or second wire segment and the second material from the coupling segment, wherein the coupling segment is a portion of the second wire segment into which the end portion of the first wire segment is inserted.

13. A wire comprising:
a first wire segment having an end portion;
a second wire segment having an end portion, one of the first and second wire segments comprising a first material; and
a coupler comprising a second material and fitted over the end portions of the first and second wire segments, and wherein the coupler is configured with at least one indent penetrating into each of the first and second wire segments, wherein at least one indent comprises a mixture of the first and second materials and no more than 30 percent of the first and second materials in the indents are brittle intermetallic phases.

14. The wire of claim 13, wherein the wire has an outer diameter, wherein the indent penetrates a penetration distance into one of the first and second wire segments, and wherein the penetration distance is no more than fifty percent of the wire outer diameter.

15. The wire of claim 13, wherein the indent is formed by welding the coupler with a laser such that a laser beam is applied directly to the coupler transverse to its axial length, and such that the laser is not applied directly to either the first or second wire segments.

* * * * *